US00RE37117E

(19) United States
(12) Reissued Patent
Palermo

(10) Patent Number: US RE37,117 E
(45) Date of Reissued Patent: Mar. 27, 2001

(54) DETACHABLE EMBOLIC COIL ASSEMBLY USING INTERLOCKING CLASPS AND METHOD OF USE

(75) Inventor: Thomas J. Palermo, San Jose, CA (US)

(73) Assignee: Target Therapeutics, Inc., Fremont, CA (US)

( * ) Notice: This patent issued on a continued prosecution application filed under 37 CFR 1.53(d), and is subject to the twenty year patent term provisions of 35 U.S.C. 154(a)(2).

(21) Appl. No.: 08/888,495

(22) Filed: Jul. 7, 1997

Related U.S. Patent Documents

Reissue of:
(64) Patent No.: 5,250,071
Issued: Oct. 5, 1993
Appl. No.: 08/949,094
Filed: Sep. 22, 1992

U.S. Applications:
(63) Continuation of application No. 08/539,781, filed on Oct. 5, 1995, now abandoned.

(51) Int. Cl.[7] ..... A61B 17/00
(52) U.S. Cl. ..... 606/1; 128/898; 606/151; 606/200
(58) Field of Search ..... 606/1, 108, 151, 606/191–200; 623/1, 11, 12; 128/898

(56) References Cited

U.S. PATENT DOCUMENTS

| | | | |
|---|---|---|---|
| 3,334,629 | | 8/1967 | Cohn . |
| 3,789,841 | | 2/1974 | Antoshkiw . |
| 4,545,390 | | 10/1985 | Leary . |
| 4,619,274 | | 10/1986 | Morrison . |
| 4,739,768 | | 4/1988 | Engelson . |
| 4,781,177 | | 11/1988 | Lebigot . |
| 4,813,934 | | 3/1989 | Engelson et al. . |
| 4,832,055 | | 5/1989 | Palestrant . |
| 4,884,579 | | 12/1989 | Engelson . |
| 4,957,501 | | 9/1990 | Lahille et al. . |
| 4,994,069 | | 2/1991 | Richart et al. . |
| 5,002,556 | | 3/1991 | Ishida et al. . |
| 5,062,829 | | 11/1991 | Pryor et al. . |
| 5,064,434 | | 11/1991 | Haber . |
| 5,098,440 | | 3/1992 | Hillstead . |
| 5,108,407 | | 4/1992 | Geremia et al. . |
| 5,109,867 | | 5/1992 | Twyford, Jr. . |
| 5,122,136 | | 6/1992 | Guglielmi et al. . |
| 5,133,731 | | 7/1992 | Butler et al. . |
| 5,167,624 | | 12/1992 | Butler et al. . |
| 5,174,276 | | 12/1992 | Crockard . |
| 5,192,301 | | 3/1993 | Kamiya et al. . |
| 5,217,484 | * | 6/1993 | Marks ..... 606/200 |
| 5,234,437 | | 8/1993 | Sepetka . |
| 5,261,916 | | 11/1993 | Engelson . |
| 5,263,964 | | 11/1993 | Purdy . |
| 5,304,195 | * | 4/1994 | Twyford et al. ..... 606/191 |
| 5,350,397 | * | 9/1994 | Palermo et al. ..... 606/108 |

FOREIGN PATENT DOCUMENTS

| | | |
|---|---|---|
| 0341039 | 3/1993 | (EP) . |
| Wo 92/14408 | 9/1992 | (WO) . |

* cited by examiner

*Primary Examiner*—Glenn K. Dawson
(74) *Attorney, Agent, or Firm*—Morrison & Foerster LLP

(57) ABSTRACT

This invention is a surgical instrument and specifically is a device for delivering an embolic coil to a selected site within the vasculature of a human body via use of a catheter. In particular, the device uses embolic coils having interlocking clasps on the coils which are secured to each other by a control wire within the catheter. Retraction of the control wire into the catheter body uncouples the distal coil.

28 Claims, 5 Drawing Sheets

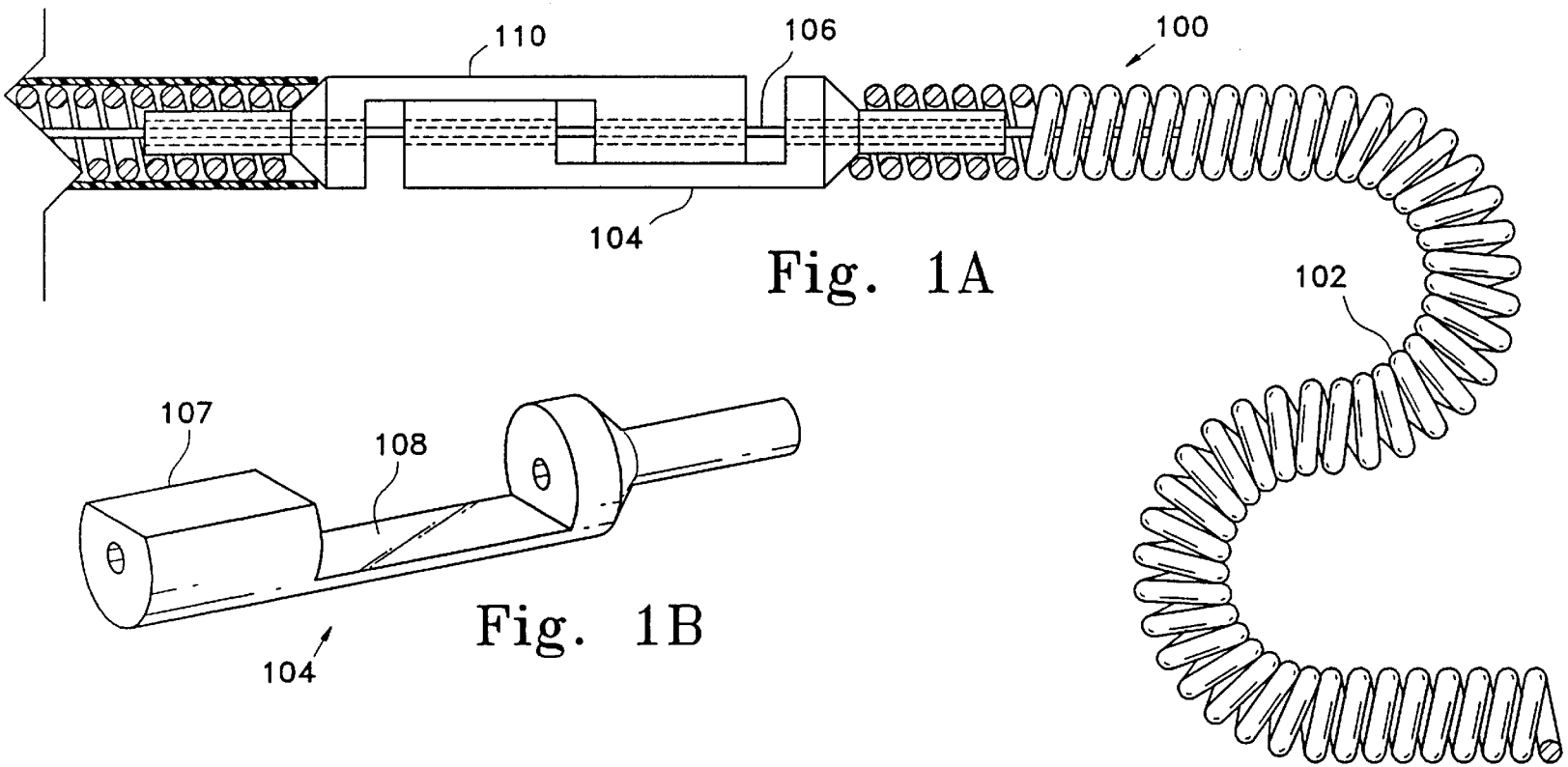
Fig. 1A
Fig. 1B
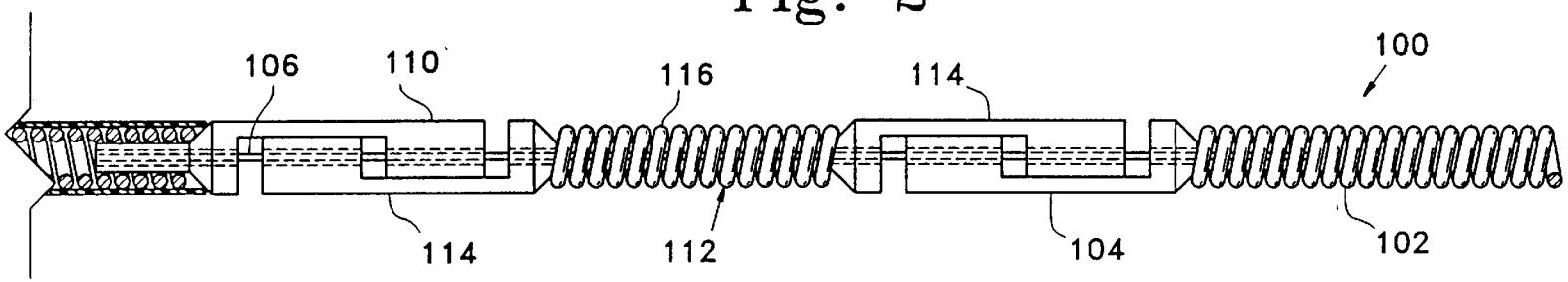
Fig. 2

106
132
120
134
130
128
134
106
132
130
128
134
106
132
130
128

DETACHABLE EMBOLIC COIL ASSEMBLY USING INTERLOCKING CLASPS AND METHOD OF USE

Matter enclosed in heavy brackets [ ] appears in the original patent but forms no part of this reissue specification; matter printed in italics indicates the additions made by reissue.

*This application is a continuation of application Ser. No. 08/539,781, filed Oct. 5, 1995, now abandoned.*

FIELD OF THE INVENTION

This invention is a surgical instrument and specifically is a device for delivering embolic coils to a selected site within the vasculature of a human body via use of a catheter. In particular, the device uses embolic coils having interlocking clasps on the coils which are secured to each other by a control wire within the catheter. Retraction of the control wire into the catheter body uncouples the distal coil.

BACKGROUND OF THE INVENTION

The endovascular treatment of a variety of vascular maladies throughout the body is an increasingly more important form of therapy. Catheters have been used to place various treatment materials, devices, and drugs within arteries and veins in the human body. Examples of these devices and their use in such treatments are shown in commonly assigned U.S. patent application Ser. Nos. 07/806,898 ("Detachable Pusher-Vasoocclusive Coil Assembly with Threaded Coupling") and 07/806,912 ("Detachable Pusher-Vasoocclusive Coil Assembly with Interlocking Ball and Keyway Coupling"). These show methods and devices for delivery of coils or wires within the human body to sites such as aneurysms, to occlude those sites. Coils such as are discussed in those two documents (as well as in U.S. Pat. No. 4,994,069), may be of a regular or helical configuration or assume a random convoluted configuration at the site. The coils normally are made of a radiopaque, biocompatible metal such as platinum, gold, tungsten, or alloys of these and other metals.

In treating aneurysms it is common to place a number of coils within the aneruysm. The coils occlude the site by posing a physical barrier to blood flow and by promoting thrombus formation at the site.

Coils have typically been placed at the desired site within the vasculature using a catheter and a pusher. The site is first accessed by the catheter. In treating peripheral or neural conditions requiring occlusion, the sites are accessed with flexible, small diameter catheters such as those shown in U.S. Pat. Nos. 4,739,768 and 4,813,934. The catheter may be guided to the site through the use of guidewires (see U.S. Pat. No. 4,884,579) or by flow-directed means such as balloons placed at the distal end of the catheter. Use of guidewires involves the placement of relatively long, torqueable proximal wire sections within the catheter attached to more flexible distal end wire sections designed to be advanced across sharp bends at vessel junctions. The guidewire is visible using x-ray and allows a catheter to be placed in extremely tortuous vessels, even though surrounded by soft tissue such as the brain.

Once the site has been reached, the catheter lumen is cleared by removing the guidewire (if a guidewire has been used), and the coil is placed into the proximal open end of the catheter and advanced through the catheter with a pusher. Pushers are wires having a distal end that is adapted to engage and push the coil through the catheter lumen as the pusher is advanced through the catheter. When the coil reaches the distal end of the catheter, it is discharged from the catheter by the pusher into the vascular site. This technique of discharging the coil from the distal end of the catheter has a number of undesirable limitation. First, because of the plunging action of the pusher and the coil, the positioning of the coil at the site cannot be controlled to a fine degree of accuracy. Second, once the coil has left the catheter, it is difficult to reposition or retrieve the coil if such is desired.

Several techniques have been developed to enable more accurate placement of coils within a vessel. In one technique (U.S. Pat. No. 5,122,136, issued Jun. 16, 1992) the coil is bonded via a metal-to-metal joint to the distal end of the pusher. The pusher and coil are made of dissimilar metals. The coil-carrying pusher is advanced through the catheter to the site and a low electrical current is passed through the pusher-coil assembly. The current causes the joint between the pusher and the coil to be severed via electrolysis. The pusher may then be retracted leaving the detached coil at an exact position within the vessel. In addition to enabling more accurate coil placement, the electric current may facilitate thrombus formation at the coil site. The only perceived disadvantage of this method is that the electrolytic release of the coil requires a period of time so that rapid detachment of the coil from the pusher does not occur.

Another technique for detaching an embolic coil is shown in commonly assigned U.S. patent application Ser. No. 07/806,912. In that document, a coil having an enlarged portion is mated with a pusher having a keyway adapted to receive the enlarged portion of the coil in an interlocking relationship is covered by a coaxial member about the pusher and the coil. The coaxial member is movable by sliding the member axially. As the coaxial member is moved away from the junction where the coil's member engages the member of the keyway of the pusher, the coil disengages and the pusher is removed.

Another device for placement of coils is shown in commonly assigned U.S. patent application Ser. No. 07/806,898. This device includes a coil having a helical portion at one end and a pusher which is threaded to the inside of the helical coil by the use of a threaded section on the outside of the pusher. The device operates to release the coil by engaging the proximal end of the coil with a sleeve while the pusher is unthreaded. Once the pusher is free, the sleeve may be used to push the coil out into the treatment area.

Another method of placing an embolic coil is shown in U.S. Pat. No. 5,108,407. This patent shows the use of a device in which embolic coils are separated from the distal end of a catheter by the use of heat-releasable adhesive bonds. The coil adheres to the therapeutic device via a mounting connection using a heat sensitive adhesive. Laser energy is transferred through a fiber optic cable, which cable terminates at the connector. The connector becomes warm and releases the adhesive bond between the connection and the coil.

None of these disclosed devices suggest the use of an interlocking latch which allows an embolic coil to be precisely positioned and then released upon retraction of a control wire positioned within that latch.

SUMMARY OF THE INVENTION

This invention is a device for placing detachable coils within the vasculature of the human body so to occlude that site with the coils. The device includes a coil that carries an interlocking clasp at at least one end of the coil, preferably at its proximal end and a pusher (positioned within the catheter) which has a clasp at its distal end which interlocks with the clasp situated on the coil. The coils may have interlocking clasps at each end thereby allowing a number of coils to be strung together and yet individually released. A control wire passing through the catheter, the pusher assembly, the pusher clasp, and the coil clasp releases the coil as the control wire is retracted through axial passageways or openings provided in the two clasps.

Another portion of the invention is a method for occluding a selected vascular site comprising the steps of: (a) accessing the site with a distal end of a catheter; (b) advancing the assembly described above through the catheter with the coil clasp and the pusher clasp interlocked to a position out the end of the distal end of the catheter; (c) withdrawing the control wire from the two clasps to thereby detach the coil from the pusher; and (d) withdrawing the catheter and pusher from the vessel.

BRIEF DESCRIPTION OF THE DRAWINGS

FIGS. 1A and 1B show, respectively, a partial sectional view of a pusher assembly and an engaged coil assembly having an interlocking clasp at only one end and a front three-quarters view of one variation of the interlocking clamp.

FIG. 2 shows a series of coil assemblies having either one or two interlocking clasps at their ends.

DESCRIPTION OF THE INVENTION

Figure 3:
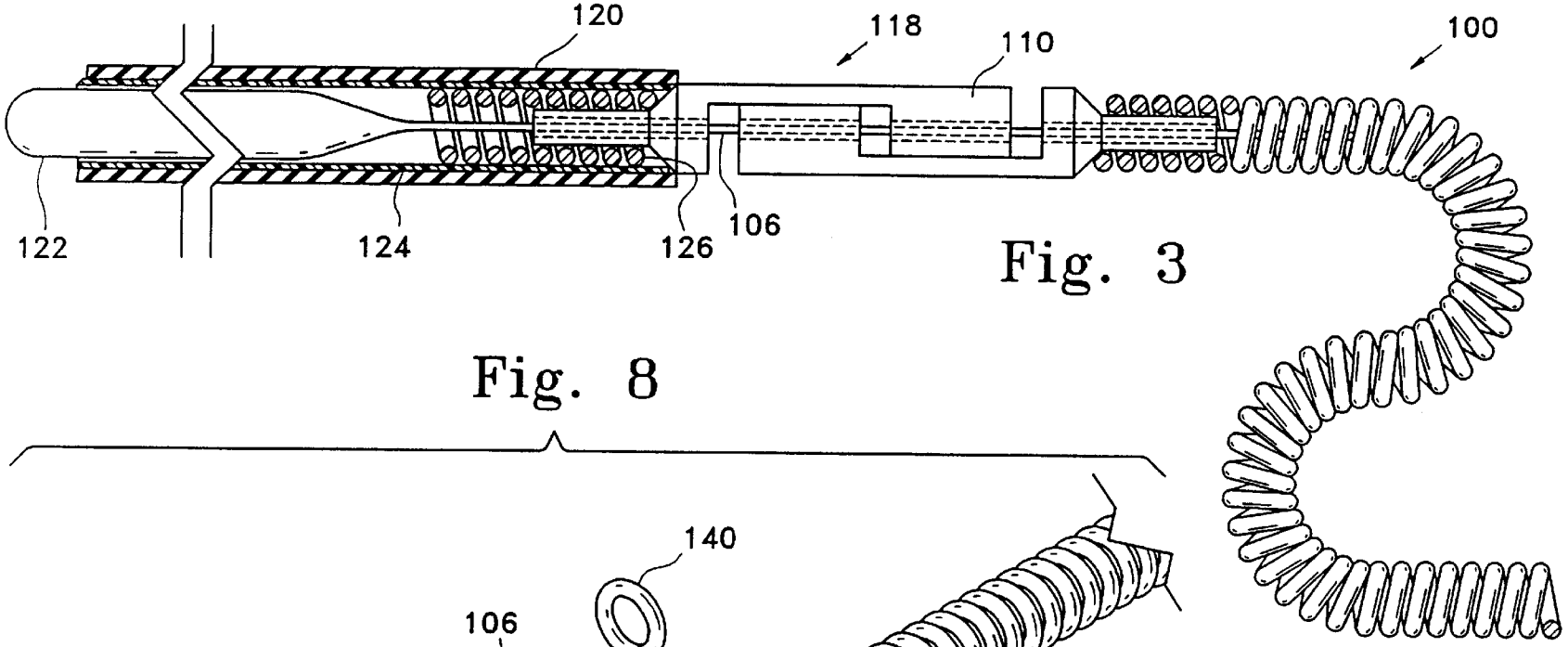
FIG. 3 shows deployment of the interlocking coil within a catheter.

The coil assembly (100) is shown in FIG. 1. The coil (102) is shown as helical in form, although it may be any other suitable form. The coil should be of a size sufficiently small that it may be advanced through a catheter that is appropriately sized for accessing the targeted vascular site. For instance, when accessing a brain aneurysm in a small vessel, an appropriately sized catheter is quite small and very flexible. The coil in such a situation must be small enough to fit through the catheter and out its distal end at the treatment site.

The coil is desirably made up of a radiopaque, physiologically compatible material. The material may be platinum, gold, tungsten, or alloys of these. Certain polymers are also suitable as coil material either alone or in conjunction with metallic markers providing radiopacity. These materials are chosen so that the procedure of locating coils within the vessel may be viewed using radiography. However, it is also contemplated that these coils may be made of various other biologically inert polymers or of carbon fiber.

The size of the coil and its constituent winding will depend upon the use to which the coil will be placed. For occluding peripheral or neural sites, the coils will typically be made of 0.05 to 0.15 mm diameter wire (platinum or platinum/tungsten alloy) that is wound to have an inner diameter of 0.15 to 1.5 mm with a minimum pitch—that is to say that the pitch is equal to the diameter of the wire used in the coil. The length of the coil will normally be in the range of 0.5 to 60 cm, preferably 0.5 to 40 cm.

If desired, the coil may be formed in such a way that the coil is essentially linear as it passes through the catheter and yet assumes a randomly oriented relaxed condition after it is released from the distal end of the catheter. A discussion of this variation may be found in U.S. Pat. No. 4,994,069.

Fixedly attached to coil (102), as is shown in FIG. 1A, is interlocking clasp (104). Interlocking clasp (104) as is depicted in the front three-quarter view in FIG. 1B, has an interior passageway allowing the control wire (106) to pass completely therethrough. As is shown in FIG. 1A, the male portion of the next adjacent interlocking clasp (110) fits into the area (108) left within clasp (104) so to allow the interlocking to take place. Said another way, the distal portion of interlocking clasp (104) is generally cylindrical in shape but has a surface (107), which may be cut or milled away, allowing the portion to mesh within the middle area (108) of an adjacent clasp. The proximal section is adapted for attaching to a coil or to a pusher assembly. The attachment may be by welding, soldering, gluing, or the like. With a control wire (106) passing through the axis of both interlocking clasps (104) and (110), the two are locked together. As is shown in FIG. 1A, the control wire may extend through the length of coil (102).

FIG. 2 shows an intermediate coil assembly (110) comprising coil (102) and interlocking clasp (104) (joined with coil assembly (112) which has interlocking clasp (114) fixedly attached at both ends of the intervening coil (116). As was the situation in FIG. 1A, the proximal interlocking clasp (114) is joined by control wire (106) with interlocking clasp (110). In this way, a significant number of coils (112) may be loaded onto a control wire (106) and delivered to the treatment site without removal of the control wire from the catheter.

FIG. 3 shows the relationship of coil assembly (100) and the pusher assembly (118) with it distal interlocking clasp (110) as it fits within catheter sheath (120). Also shown is movable inner core member (122) and the sheath (124) which fits within catheter sheath (120) and supports interlocking clasp (110). Shown in FIG. 3 is the stiffener spring (126) which provides form and support for the distal end of the pusher assembly (118) and in particular rigidly adheres to interlocking clasp (110). Inner core member (122) allows the control wire (106) to be moved axially along the interior of the catheter sheath (120) and the pusher assembly (118). Movement of the inner core member (122) in a proximal direction permits uncoupling of the coil as will be discussed in more detail below.

The length of pusher assembly (118) will be such as to be capable of being advanced entirely through the catheter to place coil (102) at the target site but yet with a sufficient portion of the proximal end of the pusher assembly (118) protruding from the proximal end of the catheter to enable the control wire (106) to be manipulated. For use in peripheral or neural surgeries, the pusher will normally about 100–200 cm in length, more normally 130–180 cm in length. The diameter of the pusher assembly (118) is usually in the range of 0.25 to about 0.90 mm.

As indicated previously, conventional catheter insertion and navigational techniques involving guidewires or flow-directed devices may be used to access the site with a catheter. Once the distal end of the catheter is positioned at the site, often by locating its distal end through the use of radiopaque marker material and radiography, the catheter is cleared. For instance, if a guidewire has been used to position the catheter, it is withdrawn from the catheter and then the pusher assembly (118) having coil assembly (100) at the distal end is advanced through the catheter. The pusher assembly (118) is advanced past the distal end of the catheter so that the coil is free of the catheter and with the coil positioned precisely at the desired treatment site.

Figures 4, 5:
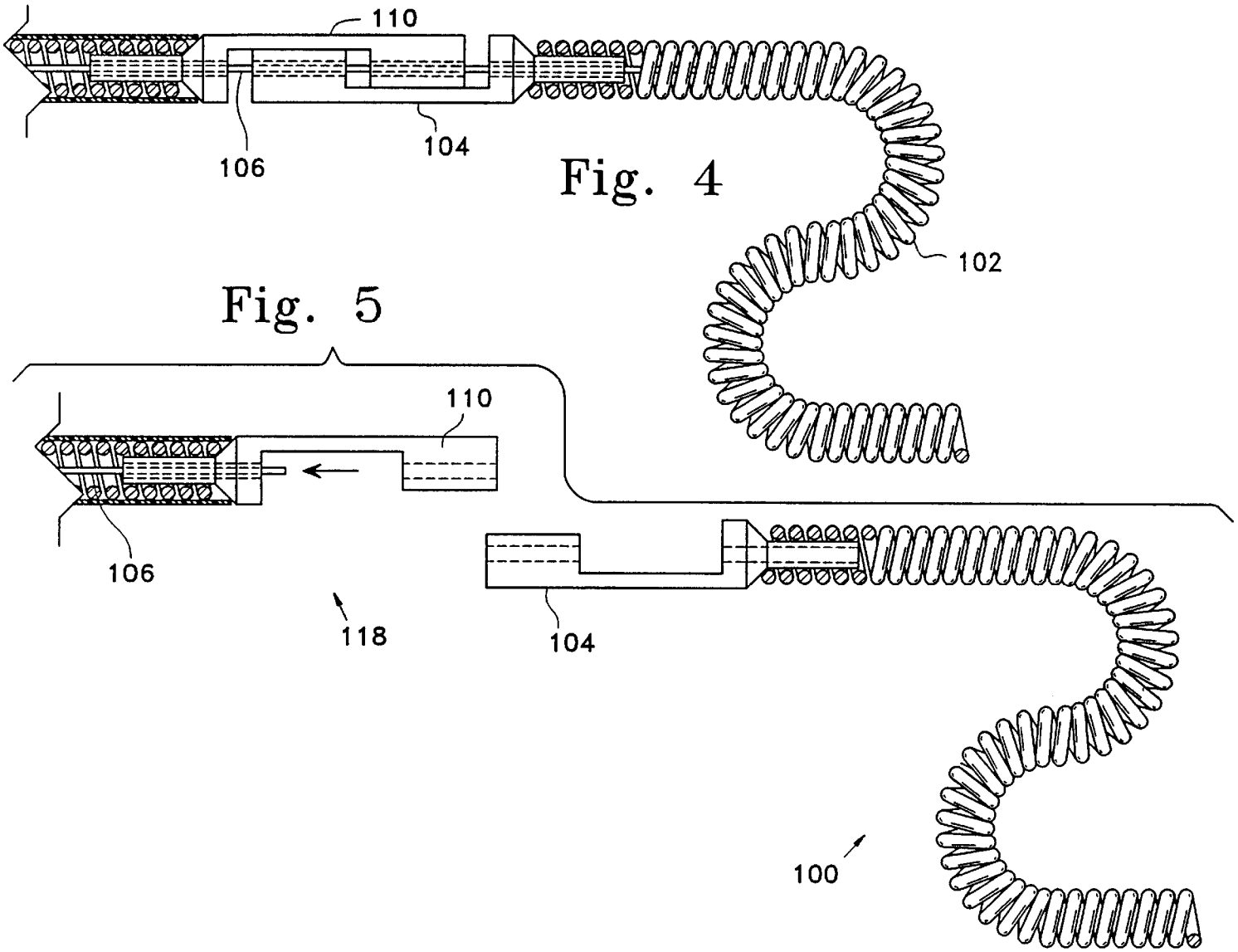
FIGS. 4 and 5 show the operation of the assembly as it places a coil within a target site.

As is shown in FIGS. 4 and 5, control wire (106) is withdrawn from the junction between coil interlocking clasp (104) and the other interlocking clasp (110). Coil assembly (100) is then free. The entire catheter may then be removed or the pusher assembly (118) may be withdrawn from the catheter lumen to provide for installation of other coils. If additional coils are to be placed at the target site, the procedure is repeated. After the desired number of coils have been placed at the site, the catheter is withdrawn from the vessel.

Figure 6A:
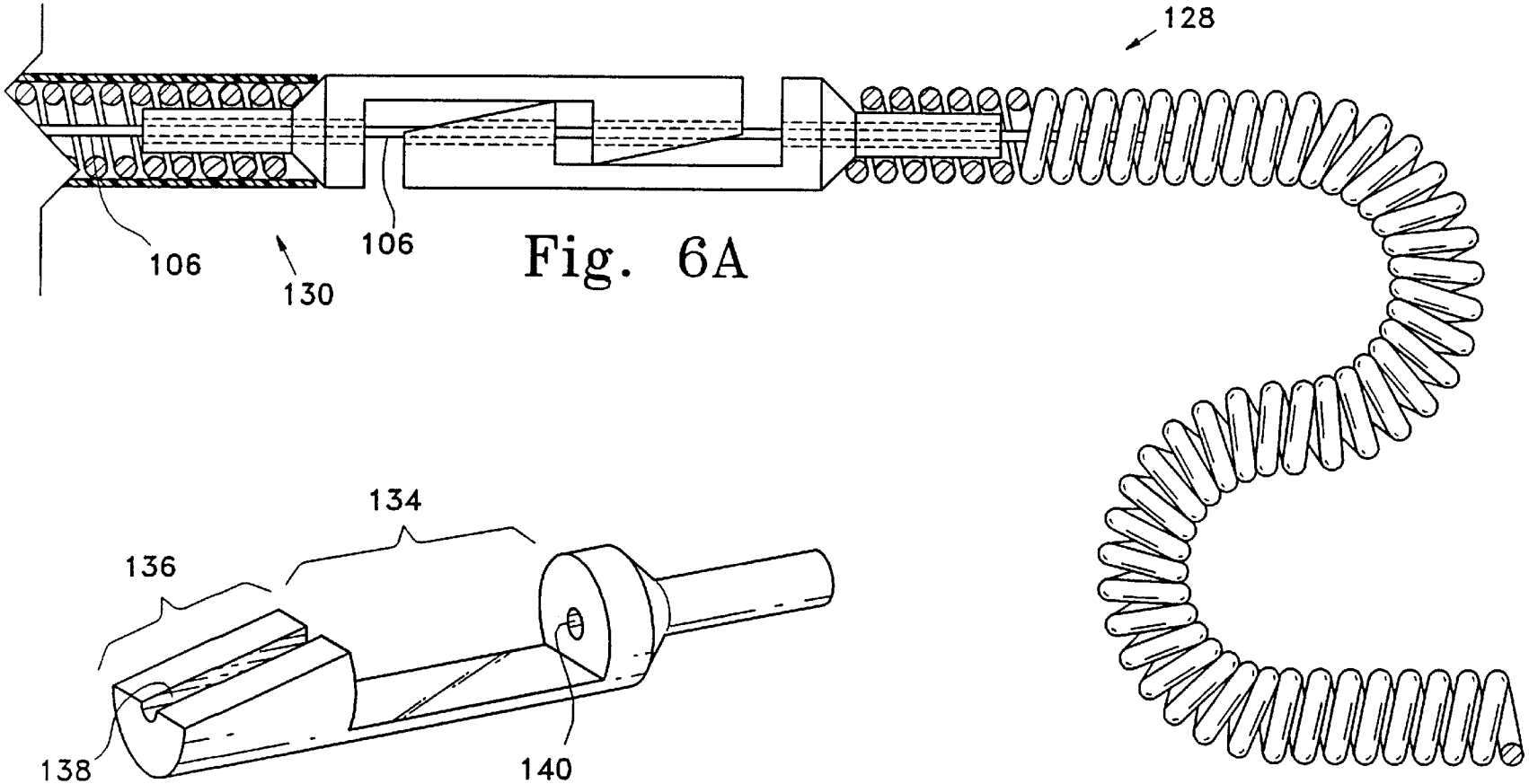
FIGS. 6A and 6B show, respectively, a partial sectional view of a pusher assembly and an engaged coil assembly having a variation of an interlocking clasp and a front three-quarter view of that variation of the interlocking clasp.
Figure 6B:
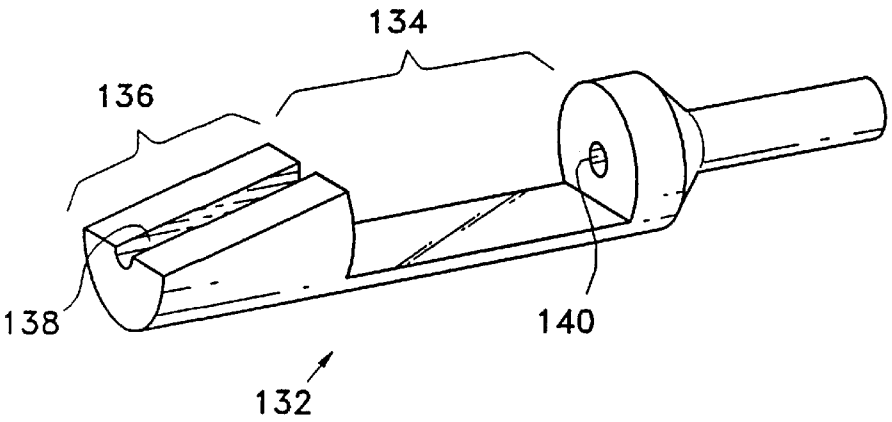

FIG. 6A shows a variation in which coil assembly (128) is interlocked with pusher assembly (130) by control wire (106). The depicted coil assembly (128) and pusher assembly (130) are different in that they incorporate the interlocking clasp (132) design shown more clearly in FIG. 6B. The interlocking clasp (132), as with the clasp depicted in FIG. 1B, utilizes an open area (134) within the clasp (132) to accept the mating ramp latch (136) from another similar clasp. The ramp latch (136) typically has a slot (138) and a passageway (140) to permit passage of the control wire through the clasp (132) from the end without obstruction.

The ramp latch (136) allows easy assembly of a string of coils within the catheter for subsequent placement using the device.

Figures 7A, 7B, 7C:
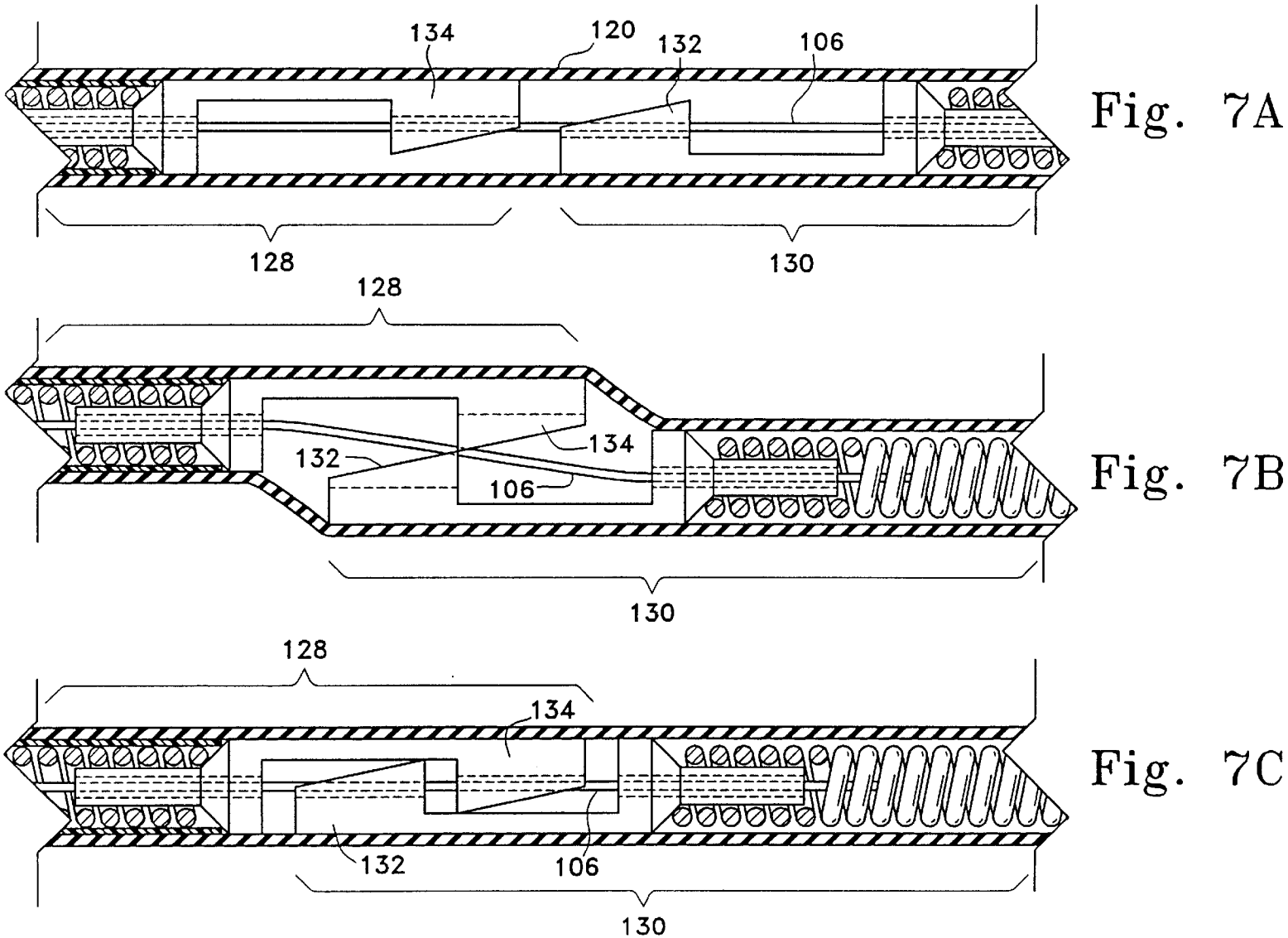
FIGS. 7A, 7B, and 7C show a method of attaching coils having the interlocking clasp shown in FIGS. 6A and 6B to a pusher body within the catheter lumen.

Such as assembly process is shown in FIGS. 7A, 7B, and 7C.

FIG. 7A shows a pusher assembly (130) approaching a coil assembly (128) which has been previously placed within a catheter sheath (120). The distal interlocking clasp (132) on the pusher assembly (130) is positioned to interlock with the proximal interlocking clasp (134) on the coil assembly (128).

FIG. 7B shows the two interlocking clasps (132 and 134) as they approach their respective ramps contacting and causing the two clasps to displace axially within the catheter sheath.

FIG. 7C shows the location of the coil assembly (128) and the pusher assembly (132) after the respective clasps are interlocked and the control wire (106) has been placed through the passageways within the clasps.

Figure 8:
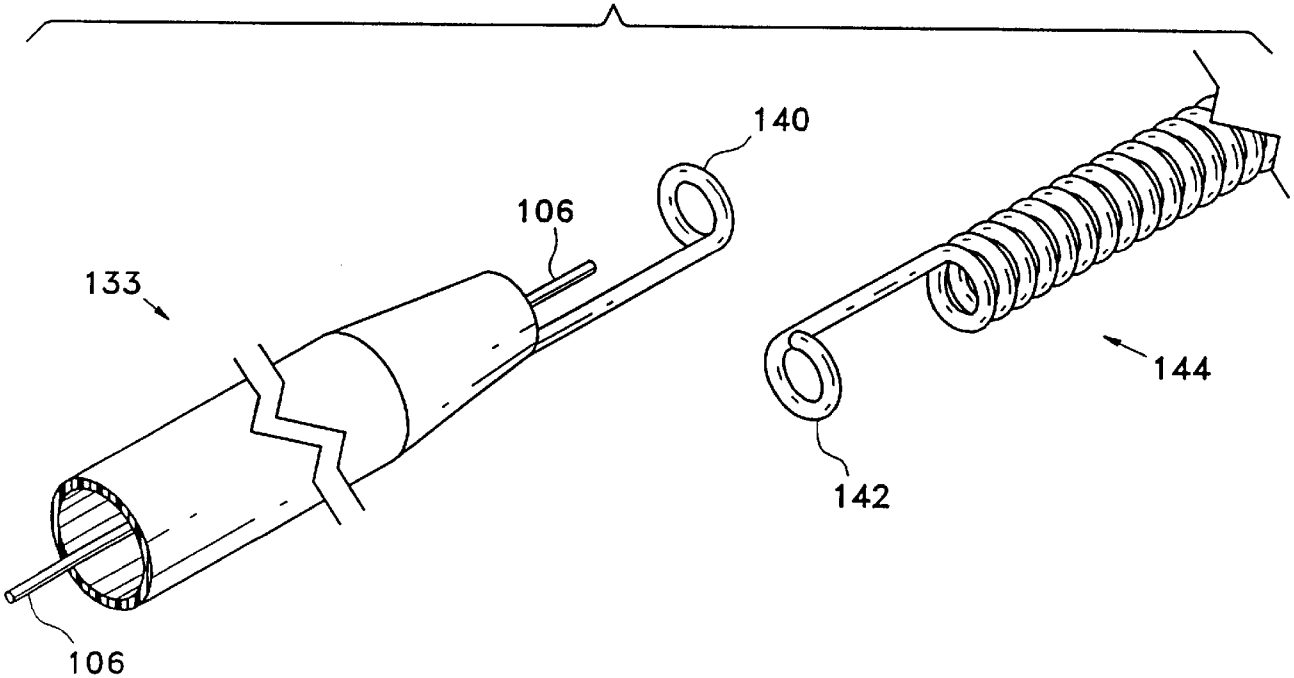
FIG. 8 shows a variation of the invention in which both the coils and the pusher body have simple loops as interlocking clasps.

FIG. 8 shows an elegantly simple variation of the invention in which the pusher (138) is a tubing member having a control wire (106) within its core. The clasp portion (140) is a simple loop comprising, e.g., wire or small rod. The corresponding interlocking loop (142) on the coil (144) forms the junction with the clasp on the pusher.

The variation of the invention shown in FIGS. 6A, 6B, 7A, 7B, 7C, and 8 may be placed within the vasculature in the same manner as shown for the variation shown in FIGS. 4 and 5.

Modifications of the device described above and methods of using it in keeping with this invention that are apparent to those having skill in this mechanical and surgical instrument design art and related fields are intended to be within the scope of the claims which follow.

I claim:

1. A detachable coil assembly for use in occluding a selected vascular site within a vessel comprising a coil having, on at least one end, [an interlocking shaped] *a first* clasp [means] having an axis and an axial passageway generally [colinear] *collinear* with the coil, the axial passageway and the [interlocking] *first* clasp [means] *shaped* to interlock with [similar shaped] *a second* clasp [means] *having a second axis and a second axial passageway* by passing a control wire through the *first and second* axial [passageway] *passageways* and to uncouple from [said similar shaped clasp means] *the second clasp* by axially withdrawing the control wire from the [shaped clasp means] *second clasp, where the first clasp comprises a middle portion shaped to accommodate a distal portion of the second clasp.*

2. The assembly of claim 1 where the coil is a helical coil.

3. The assembly of claim 2 where the coil has a random configuration.

4. The assembly of claim 2 where the coil has a straight configuration.

5. The assembly of claim 1 where the coil assembly has [interlocking shaped] *a* clasp [means] at each end.

6. The assembly of claim 1 *in combination with a second clasp, the second clasp having an axis and an axial passageway and a middle portion shaped to accommodate a distal portion of the first clasp,* in which the [interlocking shaped] *distal portion of the first* clasp [means having an axial passageway comprises a distal portion of] *and a distal portion of the second clasp each has* a generally cylindrical shape, [a middle portion adapted to accept said cylindrical distal portion from a similar interlocking shaped clasp means,] and *the first clasp further comprises* a proximal section adapted for attaching to the coil.

7. The assembly of claim 6 in which [the interlocking shaped clasp means having an axial passageway therethrough comprises a generally cylindrical distal portion having] *the generally cylindrical distal portion of each of the first and second clasps has* a ramp, *and where the distal portion of the first clasp* is adapted to engage [a] *the* ramp on [a similar interlocking shaped] *the distal portion of the second* clasp, [means, a middle portion adapted to accept a cylindrical portion with a ramp or a similar interlocking shaped clasp means, and] *the first clasp further comprising* a proximal portion adapted for attaching to the coil and having a passageway therethrough.

8. The assembly of claim 1 [additionally comprising] *in combination with* a control wire [therethrough] *through the axial passageway of the first clasp.*

9. [The assembly of] *A plurality of coil assemblies according to* claim 8 [additionally comprising one or more coil assemblies interlocked by], *where the clasp of at least a first coil assembly is interlockable with* the control wire *to the clasp of at least a second coil assembly.*

10. A combination pusher assembly-coil assembly for use in occluding a selected vascular site within a vessel comprising:

(a) a coil *with two ends* having[, on at least one end, an interlocking shaped clasp means having an axis and an axial passageway generally colinear with the coil, the axial passageway and the interlocking shaped clasp means to interlock with a similar shaped clasp means by passing a control wire through the axial passageway and to uncouple from said similar shaped clasp means by axially withdrawing the control wire from the similar clasp means] *on a first end a first clasp*;

(b) a pusher assembly [comprising] *having a distal end comprising a second clasp at the distal end, and where*

*a second end of the coil has a third clasp, and where each of the first and second clasps has an axis and an axial passageway generally colinear with the coil, the first clasp being shaped to interlock with the second clasp by passing a control wire through the first and second axial passageways and to uncouple from the second clasp by axially withdrawing the control wire from the second clasp; where the first, second and third clasps each comprises a distal portion and a middle area shaped to accommodate the distal portion of each of the other clasps, and where the distal portion and middle area of each of the first, second and third clasps are shaped such that any of the first, second and third clasps can be coupled to any of the other clasps; and where the pusher assembly comprises* a tubular pusher sheath [having] *which has* a proximal end and a distal end [and], *the pusher assembly* adapted to fit within a catheter sheath [and], *the pusher assembly* having a continuous passageway therethrough for passage of a control wire from the distal end of the pusher sheath to the proximal end of the pusher sheath[, and an interlocking shaped clasp means located at the distal end of the pusher sheath and said shaped clasp means connected to the distal end of the pusher assembly]; and (c) a control wire suitable for passage through the pusher passageway and the coil [axial passageway].

11. The [assembly] *combination* of claim 10 where the coil is a helical coil.

12. The [assembly] *combination* of claim 11 where the coil has a random configuration.

13. The [assembly] *combination* of claim 11 where the coil has a straight configuration.

14. The [assembly] *combination* of claim 10 additionally comprising a catheter sheath disposed about the pusher sheath.

15. The [assembly] *combination* of claim 10 [additionally comprising more than one coil ], *where the coil is attached to one or more additional coils via the third clasp.*

16. The [assembly] *combination* of claim 10 in which *each of* the [interlocking shaped clasp means comprise] *first and second clasps comprises* a distal portion of a generally cylindrical shape, [but having] a middle [portion adapted to accept said cylindrical] *area shaped to accommodate the* distal portion [from a similar shaped clasp means] *of the other clasp* to allow interlocking [with said similar shaped clasp means] *between the first and second clasps*, and a proximal section adapted for attaching to the coil having a passageway therethrough.

17. The [assembly] *combination* of claim 10 in which *each of* the [interlocking shaped clasp means comprise] *first and second clasps comprises* a generally cylindrical distal portion having a ramp [adapted to engage a ramp of a similar interlocking shaped clasp means,] *and* a middle [portion] *area, where the middle area is* adapted to [accept a] *accommodate the generally distal* cylindrical portion [with a ramp on a similar interlocking shaped clasp means, and] *of the other clasp, the first clasp further comprising* a proximal portion adapted for attaching to the coil and having a passageway therethrough.

18. A process for the placement of embolic coils at a selected vascular site comprising the steps of:

a) introducing to a selected site an embolic coil having, on at least one end of [said] *the* coil, [an interlocking shaped] *a first* clasp [means and] having an axis *and an axial passageway* generally colinear with the coil [and an axial passageway through the coil], the axial passageway and the [interlocking] *first* clasp [means to interlock with similar shaped clasp means] *interlocked with a second clasp* by [passing] a control wire *passing* through the axial passageway and [to uncouple] *uncoupleable* from [said similar shaped] *the second* clasp [means] by withdrawing [a] *the* control wire from the [shaped] *first* clasp [means], *where the first clasp comprises a middle portion shaped to accommodate a distal portion of the second clasp and the second clasp comprises a middle portion shaped to accommodate a distal portion of the first clasp*; and b) withdrawing the control wire from the [shaped] *first* clasp [means].

19. The process of claim 18 in which the coil is helical.

20. The process of claim 19 where the coil has a random configuration.

21. The process of claim 19 where the coil has a straight configuration.

*22. A detachable coil assembly for use in occluding a selected site within a vessel comprising a detachable coil having, on at least one end, a first clasp having an axis generally collinear with the detachable coil, the first clasp being shaped to interlock with a second clasp similar to the first clasp when the clasps overlap within a sheath, where the first clasp is a unitary piece that comprises a generally cylindrical distal portion having a flat surface configured to mesh within and abut with a flat surface in a middle portion of the second clasp, an integral middle portion shaped to accommodate a distal portion of the second clasp, and a proximal portion having a circular cross-sectional area that is larger than a non-circular cross sectional area of the first clasp middle portion, said distal portion of the second clasp having a flat surface configured to mesh within and abut with a flat surface in the middle portion of the first clasp.*

*23. The assembly of claim 22 further comprising a pusher having a second clasp on its distal end, where the first clasp comprises a generally cylindrical distal portion having a surface configured to mesh within a middle portion of the second clasp, and a middle portion shaped to accommodate a distal portion of the second clasp, said distal portion of the second clasp having a surface configured to mesh within the middle portion of the first clasp.*

*24. The assembly of claim 22 further comprising a second detachable coil having, on at least one end of the coil, a substantially cylindrical second clasp, the second clasp comprising a distal portion and a middle area, each having substantially comparable radii, where the distal portion fits a middle area of the first clasp and where the middle area fits a distal portion of the first clasp, and wherein said second clasp distal portion and said second clasp middle portion together as a whole have a generally non-cylindrical shape.*

*25. A detachable coil assembly for use in occluding a selected site within a vessel comprising a coil having, on at least one end, a first clasp with an axis and an axial passageway generally colinear with the coil, the assembly further comprising a second clasp, the first clasp being shaped to interlock with the second clasp when a control wire is passed through the axial passageway and to uncouple from the second clasp by axially withdrawing the control wire from the first clasp.*

*26. The assembly of claim 25 in combination with a pusher.*

*27. The assembly of claim 26 where the first clasp comprises a middle portion shaped to accommodate a distal portion of the second clasp and the second clasp comprises a middle portion shaped to accommodate a distal portion of the first clasp.*

*28. A detachable coil assembly for use in occluding a selected site within a vessel comprising a first coil having on*

*an end thereof a first clasp, and a second coil having on an end thereof a second clasp shaped to interlock with the first clasp, where the first clasp has an axis and an axial passageway and is adapted to interlock with the second clasp by passing a control wire through the axial passageway and a second axial passageway in said second clasp and to uncouple by axially withdrawing the control wire from at least the second axial passageway.*

* * * * *